United States Patent
Sauer et al.

(10) Patent No.: US 7,741,098 B2
(45) Date of Patent: Jun. 22, 2010

(54) **PRODUCTION OF EUKARYOTIC PROTEINS AND NUCLEIC ACID MOLECULES IN *C. ELEGANS***

(75) Inventors: Uwe H Sauer, Umea (SE); Simon Tuck, Umea (SE)

(73) Assignee: neXyte AB, Umeå (SE)

( * ) Notice: Subject to any disclaimer, the term of this patent is extended or adjusted under 35 U.S.C. 154(b) by 1045 days.

(21) Appl. No.: 10/496,767

(22) PCT Filed: Nov. 26, 2002

(86) PCT No.: PCT/SE02/02170

§ 371 (c)(1), (2), (4) Date: Sep. 8, 2004

(87) PCT Pub. No.: WO03/046188

PCT Pub. Date: Jun. 5, 2003

(65) Prior Publication Data

US 2005/0014251 A1  Jan. 20, 2005

(51) Int. Cl.
C12N 7/00 (2006.01)
C12N 7/01 (2006.01)

(52) U.S. Cl. .................................. 435/235.1

(58) Field of Classification Search ................ 435/235; 424/235

See application file for complete search history.

(56) References Cited

U.S. PATENT DOCUMENTS

| | | | | |
|---|---|---|---|---|
| 5,599,906 | A * | 2/1997 | Dasmahapatra | 530/350 |
| 5,989,868 | A * | 11/1999 | Harrison et al. | 435/69.7 |
| 6,207,147 | B1 * | 3/2001 | Hiserodt et al. | 424/93.1 |
| 6,207,417 | B1 * | 3/2001 | Zsebo et al. | 435/69.5 |
| 6,280,937 | B1 * | 8/2001 | Luo et al. | 435/6 |
| 2005/0287580 | A1 * | 12/2005 | Watt et al. | 435/6 |

FOREIGN PATENT DOCUMENTS

| | | | |
|---|---|---|---|
| WO | WO9426893 | * | 11/1994 |
| WO | WO 9426893 | * | 11/1994 |
| WO | WO 96/03502 | * | 2/1996 |
| WO | WO 9801549 | | 1/1998 |
| WO | WO 9828971 | | 7/1998 |
| WO | WO 00/54815 | * | 9/2000 |
| WO | WO 0054815 | | 9/2000 |
| WO | WO 0073510 | | 12/2000 |
| WO | WO0136674 | * | 5/2001 |
| WO | WO/01/77351 | * | 10/2001 |

OTHER PUBLICATIONS

Sheibani N. Prokaryotic gene fusion expression systems and their use in structural and functional studies of proteins Prep Biochem Biotechnol. Feb. 1999;29(1):77-90.*

Fire et al Gene 1990 vol. 93 pp. 189-198.*
Schauder et al 1989 Gene vol. 78 pp. 59-72.*
Stringham et al 1992 Molecular Biology of the Cell vol. 3 pp. 221-223.*
Mawuenyega et al 2003 vol. 2 pp. 23-25.*
(See protocol 4079 from Molecular Cloning, 3rd edition, by Joseph Sambrook and David W. Russell. Cold Spring Harbor Laboratory Press, Cold Spring Harbor, NY, USA, 2001).*
Cowing et al 1985 Proc. Natl. Acad. Sci. USA vol. 82 pp. 2679-2683.*
Fire Lab Vector Kit—Jun. 1995 (update to Aug. 1996). [retrieved on Feb. 25, 2003] Retrieved from the Internet:<URL: hhtp://ftp.ciwemb.edu/PNF:byName:/FireLabWeb/FireLabInfo/FireLabVectors/ 1995_Vector_Kit/Nec95_Docs, see p. 2, last paragraph-p. 3, first paragraph and section 'IV. Ectopic expression vectors.
Methods Cell Biol. vol. 48, 1995, Mello C. Fire A, "DNA transformation", p. 473 "VI. Directed expression of coding regions and antisense RNAs" p. 476 first paragraph.
Society of Neuroscience abstracts, vol. 26, 2000, abstract 572.15, T. Oeda et al, "A chaenorhabditis elegant model of familial amyotrophic lateral sclerosis (FALS)", pp. 1-2.
Molecular & Biochemical Parasitoloyg, vol. 112, 2000, Diane L. Redmond et al, "Expression of Haemonchus contortus pepsinogen in Caenorhabditis elegans", pp. 125-131, pp. 129-130 "Discussion".
Gene, vol. 93, 1990 Andew Fire et al, "A modular set of IacZ fusion vectors for studying gene expression in Caenorhabditis elegans", pp. 189-198.
Proc. Natl. Acad. Sci, vol. 92, 1995, Christopher D. Link, "Expression of human Beta-amyloid peptide in transgenic Caenorhabditis elegans", pp. 9368-9372.
Gross, C. A., et al., "88. Function and Regulation of the Heat Shock Proteins", In: *Escherichia coli and Salmonella—Cellular and Molecular Biology*, vol. 1, (1996), 1382-1399.

* cited by examiner

*Primary Examiner*—Robert B Mondesi
*Assistant Examiner*—Nina A Archie
(74) *Attorney, Agent, or Firm*—Schwegman, Lundberg & Woessner, P.A.

(57) ABSTRACT

Plasmid vectors for expression in *Caenorhabditis elegans* harbouring a heat inducible promoter nucleotide sequence, a synthetic intron nucleotide sequence optionally containing a Shine-Dalgarno sequence for efficient shuttling between *C. elegans* and *E. coli*, optionally a nucleotide sequence coding for a nuclear localisation signal or secretion signal, a nucleotide sequence coding for a recognizable tag, optionally a nucleotide sequence coding for a fluorescent protein, a nucleotide sequence coding for a protease cleavage site, a multiple cloning site containing a nucleotide sequence coding for an eukaryotic, such as human, protein or a nucleic acid molecule and a nucleotide sequence coding for termination of translation, are described. Methods of particularly large scale production of eukaryotic, such as human, proteins and nucleic acid molecules in nematodes are also described.

6 Claims, No Drawings

SEQUENCE LISTING

<160> NUMBER OF SEQ ID NOS: 11

<210> SEQ ID NO 1
<211> LENGTH: 3914
<212> TYPE: DNA
<213> ORGANISM: Artificial Sequence
<220> FEATURE:
<223> OTHER INFORMATION: Description of Artificial Sequence: Modified
      plasmid

<400> SEQUENCE: 1

| | | | | | | |
|---|---|---|---|---|---|---|
| atgaccatga | ttacgccaag | cttgcatgcc | tgcaggtcga | ctctagagga | tcaagagcat | 60 |
| ttgaatcaga | atatggagaa | cggagcatga | gcattttcga | agttttttag | atgcactaga | 120 |
| acaaagcgtg | ttggcttcct | ctgagcccgc | tttccttata | tacccgcatt | ctgcagcctt | 180 |
| acagaatgtt | ctagaaggtc | ctagatgcat | tcgtttgaaa | atactcccgg | tgggtgcaaa | 240 |
| gagacgcaga | cggaaaatgt | atctgggtct | ctttattgtg | tacactactt | ttccatgtac | 300 |
| cgaatgtgag | tcgccctcct | tttgcaacaa | gcagctcgaa | tgttctagaa | aaggtggaa | 360 |
| aatagtataa | ataccgttga | aaataaatac | cgaacaacat | ttgctctaat | tgtgaaatta | 420 |
| gaaatcttca | aactataatc | atctcactgg | atccccggga | ttggccaaag | gacccaaagg | 480 |
| tatgtttcga | atgatactaa | cataacatag | aacattttca | ggaggacctt | ggctagcaaa | 540 |
| atgaaacatc | accatcacca | tcaccccatg | agcgattacg | acatcccac | tactgagaat | 600 |
| ctttattttc | agggcgccat | gggcgccagg | cctcgagata | tcgatgatca | gatctggtac | 660 |
| caagctccgc | atcggccgct | gtcatcagat | cgccatctcg | cgcccgtgcc | tctgacttct | 720 |
| aagtccaatt | actcttcaac | atccctacat | gctctttctc | cctgtgctcc | caccccctat | 780 |
| ttttgttatt | atcaaaaaaa | cttcttctta | atttctttgt | ttttagctt | cttttaagtc | 840 |
| acctctaaca | atgaaattgt | gtagattcaa | aaatagaatt | aattcgtaat | aaaaagtcga | 900 |
| aaaaaattgt | gctccctccc | cccattaata | ataattctat | cccaaaatct | acacaatgtt | 960 |
| ctgtgtacac | ttcttatgtt | ttttttactt | ctgataaatt | ttttttgaaa | catcatagaa | 1020 |
| aaaaccgcac | acaaaatacc | ttatcatatg | ttacgtttca | gtttatgacc | gcaattttta | 1080 |
| tttcttcgca | cgtctgggcc | tctcatgacg | tcaaatcatg | ctcatcgtga | aaagttttg | 1140 |
| gagtatttt | ggaattttc | aatcaagtga | agtttatga | aattaatttt | cctgcttttg | 1200 |
| cttttttgggg | gtttccccta | ttgtttgtca | agagtttcga | ggacggcgtt | tttcttgcta | 1260 |
| aaatcacaag | tattgatgag | cacgatgcaa | gaaagatcgg | aagaaggttt | gggtttgagg | 1320 |
| ctcagtggaa | ggtgagtaga | agttgataat | ttgaaagtgg | agtagtgtct | atggggtttt | 1380 |
| tgccttaaat | gacagaatac | attcccaata | taccaaacat | aactgtttcc | tactagtcgg | 1440 |
| ccgtacgggc | cctttcgtct | cgcgcgtttc | ggtgatgacg | gtgaaaacct | ctgacacatg | 1500 |
| cagctcccgg | agacggtcac | agcttgtctg | taagcggatg | ccgggagcag | acaagcccgt | 1560 |
| cagggcgcgt | cagcgggtgt | tggcgggtgt | cggggctggc | ttaactatgc | ggcatcagag | 1620 |
| cagattgtac | tgagagtgca | ccatatgcgg | tgtgaaatac | cgcacagatg | cgtaaggaga | 1680 |
| aaataccgca | tcaggcggcc | ttaagggcct | cgtgatacgc | ctatttttat | aggttaatgt | 1740 |
| catgataata | atggtttctt | agacgtcagg | tggcactttt | cggggaaatg | tgcgcggaac | 1800 |
| ccctatttgt | ttatttttct | aaatacattc | aaatatgtat | ccgctcatga | gacaataacc | 1860 |
| ctgataaatg | cttcaataat | attgaaaaag | gaagagtatg | agtattcaac | atttccgtgt | 1920 |

-continued

```
cgcccttatt cccttttttg cggcattttg ccttcctgtt tttgctcacc cagaaacgct    1980
ggtgaaagta aaagatgctg aagatcagtt gggtgcacga gtgggttaca tcgaactgga    2040
tctcaacagc ggtaagatcc ttgagagttt tcgccccgaa gaacgttttc caatgatgag    2100
cacttttaaa gttctgctat gtggcgcggt attatcccgt attgacgccg ggcaagagca    2160
actcggtcgc cgcatacact attctcagaa tgacttggtt gagtactcac cagtcacaga    2220
aaagcatctt acggatggca tgacagtaag agaattatgc agtgctgcca taaccatgag    2280
tgataacact gcggccaact tacttctgac aacgatcgga ggaccgaagg agctaaccgc    2340
ttttttgcac aacatggggg atcatgtaac tcgccttgat cgttgggaac cggagctgaa    2400
tgaagccata ccaaacgacg agcgtgacac cacgatgcct gtagcaatgg caacaacgtt    2460
gcgcaaacta ttaactggcg aactacttac tctagcttcc cggcaacaat taatagactg    2520
gatggaggcg gataaagttg caggaccact tctgcgctcg gcccttccgg ctggctggtt    2580
tattgctgat aaatctggag ccggtgagcg tgggtctcgc ggtatcattg cagcactggg    2640
gccagatggt aagcccctcc cgtatcgtag ttatctacacg acggggagtc aggcaactat    2700
ggatgaacga aatagacaga tcgctgagat aggtgcctca ctgattaagc attggtaact    2760
gtcagaccaa gtttactcat atatacttta gattgattta aaacttcatt tttaatttaa    2820
aaggatctag gtgaagatcc ttttttgataa tctcatgacc aaaatccctt aacgtgagtt    2880
ttcgttccac tgagcgtcag accccgtaga aaagatcaaa ggatcttctt gagatccttt    2940
ttttctgcgc gtaatctgct gcttgcaaac aaaaaaacca ccgctaccag cggtggtttg    3000
tttgccggat caagagctac caactctttt tccgaaggta actggcttca gcagagcgca    3060
gataccaaat actgtccttc tagtgtagcc gtagttaggc caccacttca agaactctgt    3120
agcaccgcct acatacctcg ctctgctaat cctgttacca gtggctgctg ccagtggcga    3180
taagtcgtgt cttaccgggt tggactcaag acgatagtta ccggataagg cgcagcggtc    3240
gggctgaacg gggggttcgt gcacacagcc cagcttggag cgaacgacct acaccgaact    3300
gagataccta cagcgtgagc attgagaaag cgccacgctt cccgaaggga gaaaggcgga    3360
caggtatccg gtaagcggca gggtcggaac aggagagcgc acgagggagc ttccaggggg    3420
aaacgcctgg tatctttata gtcctgtcgg gtttcgccac ctctgacttg agcgtcgatt    3480
tttgtgatgc tcgtcagggg gcggagcct atggaaaaac gccagcaacg cggcctttt    3540
acggttcctg gccttttgct ggccttttgc tcacatgttc tttcctgcgt tatcccctga    3600
ttctgtggat aaccgtatta ccgcctttga gtgagctgat accgctcgcc gcagccgaac    3660
gaccgagcgc agcgagtcag tgagcgagga agcggaagag cgcccaatac gcaaaccgcc    3720
tctccccgcg cgttggccga ttcattaatg cagctgcac gacaggtttc ccgactggaa    3780
agcgggcagt gagcgcaacg caattaatgt gagttagctc actcattagg caccccaggc    3840
tttacacttt atgcttccgg ctcgtatgtt gtgtggaatt gtgagcggat aacaatttca    3900
cacaggaaac agct                                                      3914
```

<210> SEQ ID NO 2
<211> LENGTH: 3955
<212> TYPE: DNA
<213> ORGANISM: Artificial Sequence
<220> FEATURE:
<223> OTHER INFORMATION: Description of Artificial Sequence: Modified plasmid

<400> SEQUENCE: 2

```
atgaccatga ttacgccaag cttgcatgcc tgcaggtcga ctctagagga tcaagagcat      60
ttgaatcaga atatggagaa cggagcatga gcattttcga agttttttag atgcactaga     120
acaaagcgtg ttggcttcct ctgagcccgc tttccttata tacccgcatt ctgcagcctt     180
acagaatgtt ctagaaggtc ctagatgcat tcgtttgaaa atactcccgg tgggtgcaaa     240
gagacgcaga cggaaaatgt atctgggtct ctttattgtg tacactactt ttccatgtac     300
cgaatgtgag tcgccctcct tttgcaacaa gcagctcgaa tgttctagaa aaaggtggaa     360
aatagtataa ataccgttga aaataaatac cgaacaacat ttgctctaat tgtgaaatta     420
gaaatcttca aactataatc atctcactgg atccccggga ttggccaaag gacccaaagg     480
tatgtttcga atgatactaa cataacatag aacattttca ggaggaccct tggctagtgct    540
cagaaaaaat gactgctcca aagaagaagc gtaaggtgcc catgaaacat caccatcacc     600
atcaccccat gagcgattac gacatcccca ctactgagaa tctttatttt cagggcgcca     660
tgggcgccag gcctcgagat atcgatgatc agatctggta ccaagctccg catcggccgc     720
tgtcatcaga tcgccatctc gcgcccgtgc ctctgacttc taagtccaat tactcttcaa     780
catccctaca tgctctttct ccctgtgctc cacccccta ttttgttat tatcaaaaaa        840
acttcttctt aatttctttg ttttttagct tctttaagt cacctctaac aatgaaattg       900
tgtagattca aaaatagaat taattcgtaa taaaaagtcg aaaaaaattg tgctccctcc     960
ccccattaat aataattcta tcccaaaatc tacacaatgt tctgtgtaca cttcttatgt     1020
tttttttact tctgataaat tttttttgaa acatcataga aaaaaccgca cacaaaatac     1080
cttatcatat gttacgtttc agtttatgac cgcaattttt atttcttcgc acgtctgggc     1140
ctctcatgac gtcaaatcat gctcatcgtg aaaaagtttt ggagtatttt tggaatttt     1200
caatcaagtg aaagtttatg aaattaattt tcctgctttt gcttttggg ggtttcccct     1260
attgtttgtc aagagtttcg aggacggcgt ttttcttgct aaaatcacaa gtattgatga     1320
gcacgatgca agaaagatcg aagaaggtt tgggtttgag gctcagtgga aggtgagtag     1380
aagttgataa tttgaaagtg gagtagtgtc tatggggttt ttgccttaaa tgacagaata     1440
cattcccaat ataccaaaca taactgtttc ctactagtcg gccgtacggg ccctttcgtc     1500
tcgcgcgttt cggtgatgac ggtgaaaacc tctgacacat gcagctcccg gagacggtca     1560
cagcttgtct gtaagcggat gccgggagca gacaagcccg tcagggcgcg tcagcgggtg     1620
ttggcgggtg tcgggctgg cttaactatg cggcatcaga gcagattgta ctgagagtgc     1680
accatatgcg gtgtgaaata ccgcacagat gcgtaaggag aaaataccgc atcaggcggc     1740
cttaagggcc tcgtgatacg cctatttta taggttaatg tcatgataat aatggtttct     1800
tagacgtcag gtggcacttt tcggggaaat gtgcgcggaa cccctatttg tttatttttc     1860
taaatacatt caaatatgta tccgctcatg agacaataac cctgataaat gcttcaataa     1920
tattgaaaaa ggaagagtat gagtattcaa catttccgtg tcgcccttat tcccttttt     1980
gcggcatttt gccttcctgt ttttgctcac ccagaaacgc tggtgaaagt aaaagatgct     2040
gaagatcagt tgggtgcacg agtgggttac atcgaactgg atctcaacag cggtaagatc     2100
cttgagagtt ttcgccccga agaacgtttt ccaatgatga gcacttttaa agttctgcta     2160
tgtggcgcgg tattatcccg tattgacgcc gggcaagagc aactcggtcg ccgcatacac     2220
tattctcaga atgacttggt tgagtactca ccagtcacag aaaagcatct tacggatggc     2280
atgacagtaa gagaattatg cagtgctgcc ataaccatga gtgataacac tgcggccaac     2340
ttacttctga caacgatcgg aggaccgaag gagctaaccg cttttttgca aacatgggg     2400
```

```
gatcatgtaa ctcgccttga tcgttgggaa ccggagctga atgaagccat accaaacgac    2460
gagcgtgaca ccacgatgcc tgtagcaatg caacaacgt tgcgcaaact attaactggc    2520
gaactactta ctctagcttc ccggcaacaa ttaatagact ggatggaggc ggataaagtt    2580
gcaggaccac ttctgcgctc ggcccttccg gctggctggt ttattgctga taaatctgga    2640
gccggtgagc gtgggtctcg cggtatcatt gcagcactgg ggccagatgg taagccctcc    2700
cgtatcgtag ttatctacac gacggggagt caggcaacta tggatgaacg aaatagacag    2760
atcgctgaga taggtgcctc actgattaag cattggtaac tgtcagacca gtttactca    2820 tatatacttt agattgattt aaaacttcat ttttaattta aaaggatcta ggtgaagatc    2880 cttttttgata atctcatgac caaaatccct taacgtgagt tttcgttcca ctgagcgtca    2940
gaccccgtag aaaagatcaa aggatcttct tgagatcctt ttttttctgcg cgtaatctgc    3000 tgcttgcaaa caaaaaaacc accgctacca gcggtggttt gtttgccgga tcaagagcta    3060
ccaactcttt ttccgaaggt aactggcttc agcagagcgc agataccaaa tactgtcctt    3120
ctagtgtagc cgtagttagg ccaccacttc aagaactctg tagcaccgcc tacataccct    3180
gctctgctaa tcctgttacc agtggctgct gccagtggcg ataagtcgtg tcttaccggg    3240
ttggactcaa gacgatagtt accggataag gcgcagcgt cgggctgaac ggggggttcg    3300
tgcacacagc ccagcttgga gcgaacgacc tacaccgaac tgagatacct acagcgtgag    3360
cattgagaaa gcgccacgct tcccgaaggg agaaaggcgg acaggtatcc ggtaagcggc    3420
agggtcggaa caggagagcg cacgagggag cttccagggg gaaacgcctg gtatctttat    3480
agtcctgtcg ggtttcgcca cctctgactt gagcgtcgat ttttgtgatg ctcgtcaggg    3540
gggcggagcc tatggaaaaa cgccagcaac gcggcctttt tacggttcct ggccttttgc    3600
tggccttttg ctcacatgtt ctttcctgcg ttatcccctg attctgtgga taaccgtatt    3660
accgcctttg agtgagctga taccgctcgc cgcagccgaa cgaccgagcg cagcgagtca    3720
gtgagcgagg aagcggaaga gcgcccaata cgcaaaccgc ctctccccgc gcgttggccg    3780
attcattaat gcagctggca cgacaggttt cccgactgga aagcgggcag tgagcgcaac    3840
gcaattaatg tgagttagct cactcattag gcaccccagg ctttacactt tatgcttccg    3900
gctcgtatgt tgtgtggaat tgtgagcgga taacaatttc acacaggaaa cagct        3955
```

<210> SEQ ID NO 3
<211> LENGTH: 48
<212> TYPE: DNA
<213> ORGANISM: Simian virus 40

<400> SEQUENCE: 3

```
ctagtgctca gaaaaatga ctgctccaaa gaagaagcgt aaggtgcc                   48
```

<210> SEQ ID NO 4
<211> LENGTH: 2013
<212> TYPE: DNA
<213> ORGANISM: Homo sapiens

<400> SEQUENCE: 4

```
aaaccctgaa gagcccaagc aatgtggttg taaaatttgc aaaataagat taaatcttaa    60
ctgcaatctg ttaacactgc tgtctccttt cactctttct cctatatcac actttcccac   120
atgttggatg gccttggagt ggtagccata agcattttg gaattcaact aaaaaactgaa   180 ggatccttga ggacggcagt acctggcata cctacacagt cagcgttcaa caagtgtttg   240
```

-continued

```
caaaggtaca ttggggcact gggggcacga gtgatctgtg acaatatccc tggtttggtg         300
agccggcagc ggcagctgtg ccagcgttac ccagacatca tgcgttcagt gggcgagggt         360
gcccgagaat ggatccgaga gtgtcagcac caattccgcc accaccgctg aactgtacc          420 accctggacc gggaccacac cgtctttggc cgtgtcatgc tcagaagtag ccagagggca         480
gcttttgtat atgccatctc atcagcaggg gtagtccacg ctattactcg cgcctgtagc         540
cagggtgaac tgagtgtgtg cagctgtgac ccctacaccc gtggccgaca ccatgaccag         600
cgtggggact ttgactgggg tggctgcagt gacaacatcc actacggtgt ccgttttgcc         660
aaggccttcg tggatgccaa ggagaagagg cttaaggatg cccgggccct catgaactta         720
cataataacc gctgtggtcg cacggctgtg cggcggtttc tgaagctgga gtgtaagtgc         780 catgcgtga gtggttcctg tactctgcgc acctgctggc gtgcactctc agatttccgc          840
cgcacaggtg attacctgcg gcgacgctat gatgggctg tgcaggtgat ggccacccaa          900
gatggtgcca acttcaccgc agcccgccaa ggctatcgcc gtgccacccg gactgatctt         960
gtctactttg caactctcc agattactgt gtcttggaca aggctgcagg ttccctaggc         1020
actgcaggcc gtgtctgcag caagacatca aaaggaacag acggttgtga atcatgtgc         1080 tgtggccgag ggtacgacac aactcgagtc accgtgtta cccagtgtga gtgcaaattc         1140
cactggtgct gtgctgtacg gtgcaaggaa tgcagaaata ctgtggacgt ccatacttgc        1200
aaagccccca agaaggcaga gtggctggac caaacctgaa cacacagata cctcactcat        1260
ccctccaatt caagcctctc aactcaaaag cacaagatcc ttgcatgcac accttcctcc       1320
accctccacc ctgggctgct accgcttcta tttaaggatg tagagagtaa tccatgggga      1380
ccatggtgtc ctggctggtt ccttagccct gggaaggagt tgtcagggga tataagaaac      1440
tgagcaagct ccctgatttc ccgctctgga gatttgaagg gagagtagaa gagatagggg      1500
gtctttagag tgaaatgagt tgcactaaag tacgtagttg aggctccttt tttctttcct      1560
ttgcaccagc ttcccgatac ttcttggtgt gcaagaggaa gggtacctgt agagagcttc      1620
tttttgtttc tacctggcca aagttagatg ggacaaagat gaatggcatg tcccttctct      1680
gaagtccgtt tgagcagaac tacctggtac cccgaaagaa aatcttaggc taccacattc      1740
tattattgag agcctgagat gttagccata gtggacaagg ttccattcac atgctcatat      1800
gtttataaac tgtgttttgt agaagaaaaa gaatcataac aatacaaaca cacattcatt      1860
ctctcttttt ctctctacca ttctcaacct gtattggaca gcactgcctc ttttgcttac      1920
ttgctgcctg ttcaaactga ggtggaatgc agtggttccc atgcttaaca aatcattaaa      1980
acaccctaga acactcctag gatagattaa tgt                                    2013
```

<210> SEQ ID NO 5
<211> LENGTH: 1584
<212> TYPE: DNA
<213> ORGANISM: Homo sapiens

<400> SEQUENCE: 5

```
ggggagagga agagtggtag ggggagggag agagagagga agagtttcca aacttgtctc          60
cagtgacagg agacatttac gttccacaag ataaaactgc cacttagagc ccagggaagc         120
taaaccttcc tggcttggcc taggagctcg agcggagtca tgggctctct ggtcctgaca         180
ctgtgcgctc ttttctgcct ggcagcttac ttggtttctg gcagccccat catgaaccta         240
gagcagtctc ctctggaaga agatatgtcc ctctttggtg atgttttctc agagcaagac         300
ggtgtcgact ttaacacact gctccagagc atgaaggatg agtttcttaa gacactaaac         360
```

```
ctctctgaca tccccacgca ggattcagcc aaggtggacc caccagagta catgttggaa      420
ctctacaaca aatttgcaac agatcggacc tccatgccct ctgccaacat cattaggagt      480
ttcaagaatg aagatctgtt ttcccagccg gtcagtttta atgggctccg aaaataccccc     540
ctcctcttca atgtgtccat tcctcaccat gaagaggtca tcatggctga acttaggcta      600
tacacactgg tgcaaaggga tcgtatgata tacgatggag tagaccggaa aattaccatt      660
tttgaagtgc tggagagcaa aggggataat gagggagaaa gaaacatgct ggtcttggtg      720
tctggggaga tatatggaac caacagtgag tgggagactt ttgatgtcac agatgccatc      780
agacgttggc aaaagtcagg ctcatccacc caccagctgg aggtccacat tgagagcaaa      840
cacgatgaag ctgaggatgc cagcagtgga cggctagaaa tagataccag tgcccagaat      900
aagcataacc ctttgctcat cgtgttttct gatgaccaaa gcagtgacaa ggagaggaag      960
gaggaactga atgaaatgat tcccatgag caacttccag agctggacaa cttgggcctg     1020
gatagctttt ccagtggacc tggggaagag gctttgttgc agatgagatc aaacatcatc     1080
tatgactcca ctgcccgaat cagaaggaac gccaaaggaa actactgtaa gaggaccccg     1140
ctctacatcg acttcaagga gattgggtgg gactcctgga tcatcgctcc gcctggatac     1200
gaagcctatg aatgccgtgg tgtttgtaac taccccctgg cagagcatct cacacccaca     1260
aagcatgcaa ttatccaggc cttggtccac ctcaagaatt cccagaaagc ttccaaagcc     1320
tgctgtgtgc ccacaaagct agagcccatc tccatcctct atttagacaa aggcgtcgtc     1380
acctacaagt ttaaatacga aggcatggcc gtctccgaat gtggctgtag atagaagaag     1440
agtcctatgg cttatttaat aactgtaaat gtgtatattt ggtgttccta tttaatgaga     1500
ttatttaata agggtgtaca gtaatagagg cttgctgcct tcaggaaatg gacaggtcag     1560
tttgttgtag gaaatgcata tttt                                            1584

<210> SEQ ID NO 6
<211> LENGTH: 889
<212> TYPE: DNA
<213> ORGANISM: Homo sapiens

<400> SEQUENCE: 6
cagtggagag ggcgctgcgc tcgggctacc caatgcgtgg actatctgcc gccgctgttc       60
gtgcaatatg ctggagctcc agaacagcta aacggagtcg ccacaccact gtttgtgctg      120
gatcgcagcg ctgcctttcc ttatgaagaa gacacaaact tggattctca cttgcattta      180
tcttcagctg ctcctatttta atcctctcgt caaaactgaa gggatctgca ggaatcgtgt      240
gactaataat gtaaaagacg tcactaaatt ggtggcaaat cttccaaaag actacatgat      300
aaccctcaaa tatgtccccg ggatggatgt tttgccaagt cattgttgga taagcgagat      360
ggtagtacaa ttgtcagaca gcttgactga tcttctggac aagttttcaa atatttctga      420
aggcttgagt aattattcca tcatagacaa acttgtgaat atagtggatg accttgtgga      480
gtgcgtgaaa gaaaactcat ctaaggatct aaaaaaatca ttcaagagcc cagaacccag      540
gctctttact cctgaagaat tctttagaat ttttaataga tccattgatg ccttcaagga      600
ctttgtagtg gcatctgaaa ctagtgattg tgtggtttct tcaacattaa gtcctgagaa      660
agggaaggcc aaaaatcccc ctggagactc cagcctacac tgggcagcca tggcattgcc      720
agcattgttt tctcttataa ttggctttgc ttttggagcc ttatactgga agaagagaca      780
gccaagtctt acaagggcag ttgaaaatat acaaattaat gaagaggata atgagataag      840
```
tatgttgcaa gagaaagaga gagagtttca agaagtgtaa ttgtggctt            889

<210> SEQ ID NO 7
<211> LENGTH: 627
<212> TYPE: DNA
<213> ORGANISM: Homo sapiens

<400> SEQUENCE: 7
atgtggaaat ggatactgac acattgtgcc tcagcctttc cccacctgcc cggctgctgc     60
tgctgctgct ttttgttgct gttcttggtg tcttccgtcc ctgtcacctg ccaagccctt    120
ggtcaggaca tggtgtcacc agaggccacc aactcttctt cctcctcctt ctcctctcct    180
tccagcgcgg gaaggcatgt gcggagctac aatcaccttc aaggagatgt ccgctggaga    240
aagctattct ctttcaccaa gtactttctc aagattgaga gaacgggaa ggtcagcggg      300
accaagaagg agaactgccc gtacagcatc ctggagataa catcagtaga aatcggagct    360
gttgccgtca aagccattaa cagcaactat tacttagcca ggaacaagaa ggggaaactc    420
tatggctcaa agaatttaa caatgactgt aagctgaagg agaggataga ggaaaatgga      480
tacaataccct atgcatcatt taactggcag cataatggga ggcaaatgta tgtggcattg    540
aatggaaaag gagctccaag gagaggacag aaaacacgaa ggaaaaacac ctctgctcac    600
tttcttccaa tggtggtaca ctcatag                                         627

<210> SEQ ID NO 8
<211> LENGTH: 870
<212> TYPE: DNA
<213> ORGANISM: Artificial Sequence
<220> FEATURE:
<223> OTHER INFORMATION: Description of Artificial Sequence: green
      fluorescent proten encoding sequence

<400> SEQUENCE: 8
atgagtaaag gagaagaact tttcactgga gttgtcccaa ttcttgttga attagatggt     60
gatgttaatg ggcacaaatt ttctgtcagt ggagagggtg aaggtgatgc aacatacgga   120
aaacttaccc ttaaatttat ttgcactact ggaaaactac ctgttccatg gtaagttta     180
aacatatata tactaactaa ccctgattat ttaaattttc agccaacact tgtcactact    240
ttctgttatg tgttcaatg cttctcgaga tacccagatc atatgaaacg gcatgacttt    300
ttcaagagtg ccatgcccga aggttatgta caggaaagaa ctatattttt caaagatgac   360
gggaactaca agacacgtaa gtttaaacag ttcggtacta actaaccata catatttaaa    420
ttttcaggtg ctgaagtcaa gtttgaaggt gataccettg ttaatagaat cgagttaaaa    480
ggtattgatt ttaaagaaga tggaaacatt cttggacaca aattggaata caactataac    540
tcacacaatg tatacatcat ggcagacaaa caaaagaatg gaatcaaagt tgtaagttta   600
aacttggact tactaactaa cggattatat ttaaattttc agaacttcaa aattagacac    660
aacattgaag atggaagcgt tcaactagca gaccattatc aacaaaatac tccaattggc    720
gatggccctg tccttttacc agacaaccat tacctgtcca cacaatctgc cctttcgaaa    780
gatcccaacg aaaagagaga ccacatggtc cttcttgagt ttgtaacagc tgctgggatt    840
acacatggca tggatgaact atacaaatag                                     870

<210> SEQ ID NO 9
<211> LENGTH: 4718
<212> TYPE: DNA
<213> ORGANISM: Artificial Sequence
<220> FEATURE:

<223> OTHER INFORMATION: Description of Artificial Sequence: Modified plasmid

<400> SEQUENCE: 9

```
atgaccatga ttacgccaag cttgcatgcc tgcaggtcga ctctagagga tcaagagcat    60
ttgaatcaga atatggagaa cggagcatga gcattttcga agttttttag atgcactaga   120
acaaagcgtg ttggcttcct ctgagcccgc tttccttata tacccgcatt ctgcagcctt   180
acagaatgtt ctagaaggtc ctagatgcat tcgtttgaaa atactcccgg tgggtgcaaa   240
gagacgcaga cggaaaatgt atctgggtct ctttattgtg tacactactt ttccatgtac   300
cgaatgtgag tcgccctcct tttgcaacaa gcagctcgaa tgttctagaa aaggtggaa    360
aatagtataa ataccgttga aaataaatac gaacaacat ttgctctaat tgtgaaatta    420
gaaatcttca aactataatc atctcactgg atccccggga ttggccaaag acccaaagg    480
tatgtttcga atgatactaa cataacatag aacattttca ggaggaccct tggctagcga   540
attcaaaatg atatcagaga atctttattt tcagggcagt aaaggagaag aacttttcac   600
tggagttgtc ccaattcttg ttgaattaga tggtgatgtt aatgggcaca aattttctgt   660
cagtggagag ggtgaaggtg atgcaacata cggaaaactt acccttaaat ttatttgcac   720
tactggaaaa ctacctgttc catgggtaag tttaaacata tatatactaa ctaaccctga   780
ttatttaaat tttcagccaa cacttgtcac tactttctgt tatggtgttc aatgcttctc   840
gagatacccca gatcatatga aacggcatga cttttttcaag agtgccatgc ccgaaggtta   900
tgtacaggaa agaactatat ttttcaaaga tgacgggaac tacaagacac gtaagtttaa   960
acagttcggt actaactaac catacatatt taaattttca ggtgctgaag tcaagtttga  1020
aggtgatacc cttgttaata gaatcgagtt aaaaggtatt gattttaaag aagatggaaa  1080
cattcttgga cacaaattgg aatacaacta taactcacac aatgtataca tcatggcaga  1140
caaacaaaag aatggaatca agttgtaagt tttaaacttg gacttactaa ctaacggatt  1200
atatttaaat tttcagaact tcaaaattag acacaacatt gaagatggaa gcgttcaact  1260
agcagaccat tatcaacaaa atactccaat tggcgatggc cctgtccttt taccagacaa  1320
ccattacctg tccacacaat ctgccctttc gaaagatccc aacgaaaaga gagaccacat  1380
ggtccttctt gagtttgtaa cagctgctgg gattacacat ggcatggatg aactatacaa  1440
acatcaccat caccatcact aatgagagct ccgcatcggc cgctgtcatc agatcgccat  1500
ctcgcgcccg tgcctctgac ttctaagtcc aattactctt caacatccct acatgctctt  1560
tctccctgtg ctcccacccc ctattttgt tattatcaaa aaacttctt cttaatttct   1620
ttgttttta gcttctttta agtcacctct aacaatgaaa ttgtgtagat tcaaaaatag  1680
aattaattcg taataaaaag tcgaaaaaaa ttgtgctccc tcccccatt aataataatt   1740
ctatcccaaa atctacacaa tgttctgtgt acacttctta tgttttttt acttctgata  1800
aattttttt gaaacatcat agaaaaaacc gcacacaaaa taccttatca tatgttacgt   1860
ttcagtttat gaccgcaatt tttatttctt cgcacgtctg ggcctctcat gacgtcaaat  1920
catgctcatc gtgaaaaagt tttggagtat ttttggaatt tttcaatcaa gtgaaagttt  1980
atgaaattaa ttttcctgct tttgcttttt gggggtttcc cctattgttt gtcaagagtt  2040
tcgaggacgg cgttttctt gctaaaatca caagtattga tgagcacgat gcaagaaga   2100
tcggaagaag gtttgggttt gaggctcagt ggaaggtgag tagaagttga aatttgaaa   2160
gtggagtagt gtctatgggg ttttgccttt aaatgacaga atacattccc aatataccaa  2220
```

```
acataactgt tcctactag tcggccgtac gggcccttc gtctcgcgcg tttcggtgat    2280
gacggtgaaa acctctgaca catgcagctc ccggagacgg tcacagcttg tctgtaagcg    2340
gatgccggga gcagacaagc ccgtcagggc gcgtcagcgg gtgttggcgg gtgtcgggc    2400 tggcttaact atgcggcatc agagcagatt gtactgagag tgcaccatat gcggtgtgaa    2460
ataccgcaca gatgcgtaag gagaaaatac cgcatcaggc ggccttaagg gcctcgtgat    2520
acgcctattt ttataggtta atgtcatgat aataatggtt tcttagacgt caggtggcac    2580
ttttcgggga atgtgcgcg gaaccctat tgtttattt ttctaaatac attcaaatat    2640
gtatccgctc atgagacaat aaccctgata atgcttcaa taatattgaa aaggaagag    2700 tatgagtatt caacatttcc gtgtcgccct tattcccttt tttgcggcat tttgccttcc    2760 tgttttgct cacccagaaa cgctggtgaa agtaaaagat gctgaagatc agttgggtgc    2820
acgagtgggt tacatcgaac tggatctcaa cagcggtaag atccttgaga gttttcgccc    2880
cgaagaacgt tttccaatga tgagcacttt taaagttctg ctatgtggcg cggtattatc    2940
ccgtattgac gccgggcaag agcaactcgg tcgccgcata cactattctc agaatgactt    3000
ggttgagtac tcaccagtca cagaaaagca tcttacggat ggcatgacag taagagaatt    3060
atgcagtgct gccataacca tgagtgataa cactgcggcc aacttacttc tgacaacgat    3120
cggaggaccg aaggagctaa ccgctttttt gcacaacatg gggatcatg taactcgcct    3180 tgatcgttgg gaaccggagc tgaatgaagc cataccaaac gacgagcgtg acaccacgat    3240
gcctgtagca atggcaacaa cgttgcgcaa actattaact ggcgaactac ttactctagc    3300
ttcccggcaa caattaatag actggatgga ggcggataaa gttgcaggac cacttctgcg    3360
ctcggccctt ccggctggct ggtttattgc tgataaatct ggagccggtg agcgtgggtc    3420
tcgcggtatc attgcagcac tggggccaga tggtaagccc tcccgtatcg tagttatcta    3480
cacgacgggg agtcaggcaa ctatggatga acgaaataga cagatcgctg agataggtgc    3540
ctcactgatt aagcattggt aactgtcaga ccaagtttac tcatatatac tttagattga    3600
tttaaaactt catttttaat ttaaaaggat ctaggtgaag atccttttg ataatctcat    3660 gaccaaaatc ccttaacgtg agttttcgtt ccactgagcg tcagacccg tagaaaagat    3720 caaaggatct tcttgagatc ctttttttct gcgcgtaatc tgctgcttgc aaacaaaaaa    3780
accaccgcta ccagcggtgg tttgtttgcc ggatcaagag ctaccaactc ttttttccgaa    3840 ggtaactggc ttcagcagag cgcagatacc aaatactgtc cttctagtgt agccgtagtt    3900
aggccaccac ttcaagaact ctgtagcacc gcctacatac ctcgctctgc taatcctgtt    3960
accagtggct gctgccagtg gcgataagtc gtgtcttacc gggttggact caagacgata    4020
gttaccggat aaggcgcagc ggtcgggctg aacggggggt tcgtgcacac agcccagctt    4080
ggagcgaacg acctacaccg aactgagata cctacagcgt gagcattgag aaagcgccac    4140
gcttcccgaa gggagaaagg cggacaggta tccggtaagc ggcagggtcg gaacaggaga    4200
gcgcacgagg gagcttccag ggggaaacgc ctggtatctt tatagtcctg tcgggtttcg    4260
ccacctctga cttgagcgtc gatttttgtg atgctcgtca gggggcgga gcctatggaa    4320 aaacgccagc aacgcggcct ttttacggtt cctggccttt tgctggcctt tgctcacat    4380 gttcttcct gcgttatccc ctgattctgt ggataaccgt attaccgcct tgagtgagc    4440 tgataccgct cgccgcagcc gaacgaccga gcgcagcgag tcagtgagcg aggaagcgga    4500
agagcgccca atacgcaaac cgcctctccc cgcgcgttgg ccgattcatt aatgcagctg    4560
gcacgacagg tttcccgact ggaaagcggg cagtgagcgc aacgcaatta atgtgagtta    4620
```

| | |
|---|---|
| gctcactcat taggcacccc aggctttaca ctttatgctt ccggctcgta tgttgtgtgg | 4680 |
| aattgtgagc ggataacaat ttcacacagg aaacagct | 4718 |

<210> SEQ ID NO 10
<211> LENGTH: 4754
<212> TYPE: DNA
<213> ORGANISM: Artificial Sequence
<220> FEATURE:
<223> OTHER INFORMATION: Description of Artificial Sequence: Modified plasmid

<400> SEQUENCE: 10

| | |
|---|---|
| atgaccatga ttacgccaag cttgcatgcc tgcaggtcga ctctagagga tcaagagcat | 60 |
| ttgaatcaga atatggagaa cggagcatga gcattttcga agtttttag atgcactaga | 120 |
| acaaagcgtg ttggcttcct ctgagcccgc tttccttata tacccgcatt ctgcagcctt | 180 |
| acagaatgtt ctagaaggtc ctagatgcat tcgtttgaaa atactcccgg tgggtgcaaa | 240 |
| gagacgcaga cggaaaatgt atctgggtct ctttattgtg tacactactt ttccatgtac | 300 |
| cgaatgtgag tcgccctcct tttgcaacaa gcagctcgaa tgttctagaa aaggtggaa | 360 |
| aatagtataa ataccgttga aaataaatac cgaacaacat ttgctctaat tgtgaaatta | 420 |
| gaaatcttca aactataatc atctcactgg atccccggga ttggccaaag acccaaagg | 480 |
| tatgtttcga atgatactaa cataacatag aacattttca ggaggaccct ggctagcga | 540 |
| attcaaaatg atatcagaga atctttattt tcagggcagt aaaggagaag aacttttcac | 600 |
| tggagttgtc ccaattcttg ttgaattaga tggtgatgtt aatgggcaca aattttctgt | 660 |
| cagtggagag ggtgaaggtg atgcaacata cggaaaactt acccttaaat ttatttgcac | 720 |
| tactggaaaa ctacctgttc catgggtaag tttaaacata tatactaa ctaaccctga | 780 |
| ttatttaaat tttcagccaa cacttgtcac tactttctgt tatggtgttc aatgcttctc | 840 |
| gagataccca gatcatatga acggcatga cttttcaag agtgccatgc ccgaaggtta | 900 |
| tgtacaggaa agaactatat ttttcaaaga tgacgggaac tacaagacac gtaagtttaa | 960 |
| acagttcggt actaactaac catacatatt taaattttca ggtgctgaag tcaagtttga | 1020 |
| aggtgatacc cttgttaata gaatcgagtt aaaaggtatt gattttaaag aagatggaaa | 1080 |
| cattcttgga cacaaattgg aatacaacta taactcacac aatgtataca tcatggcaga | 1140 |
| caaacaaaag aatggaatca agttgtaag tttaaacttg gacttactaa ctaacggatt | 1200 |
| atatttaaat tttcagaact tcaaaattag acacaacatt gaagatggaa gcgttcaact | 1260 |
| agcagaccat tatcaacaaa atactccaat tggcgatggc cctgtccttt taccagacaa | 1320 |
| ccattacctg tccacacaat ctgccctttc gaaagatccc aacgaaaaga gagaccacat | 1380 |
| ggtccttctt gagtttgtaa cagctgctgg gattacacat ggcatggatg aactatacaa | 1440 |
| aactgctcca agaagaagc gtaaggtgcc catgaaacat caccatcacc atcactaatg | 1500 |
| agagctccgc atcggccgct gtcatcagat cgccatctcg cgccgtgcc tctgacttct | 1560 |
| aagtccaatt actcttcaac atccctacat gctctttctc cctgtgctcc cacccctat | 1620 |
| ttttgttatt atcaaaaaaa cttcttctta atttctttgt ttttagctt cttttaagtc | 1680 |
| acctctaaca atgaaattgt gtagattcaa aaatagaatt aattcgtaat aaaaagtcga | 1740 |
| aaaaaattgt gctccctccc ccattaata ataattctat cccaaaatct acacaatgtt | 1800 |
| ctgtgtacac ttcttatgtt tttttactt ctgataaatt tttttgaaa catcatagaa | 1860 |
| aaaccgcac acaaaatacc ttatcatatg ttacgtttca gtttatgacc gcaatttta | 1920 |

```
tttcttcgca cgtctgggcc tctcatgacg tcaaatcatg ctcatcgtga aaaagttttg    1980
gagtatttt  ggaattttc  aatcaagtga aagtttatga aattaattt  cctgcttttg    2040
cttttgggg  gtttcccta  ttgtttgtca agagtttcga ggacggcgtt tttcttgcta    2100
aaatcacaag tattgatgag cacgatgcaa gaaagatcgg aagaaggttt gggtttgagg    2160
ctcagtggaa ggtgagtaga agttgataat ttgaaagtgg agtagtgtct atggggtttt    2220
tgccttaaat gacagaatac attcccaata taccaaacat aactgtttcc tactagtcgg    2280
ccgtacgggc cctttcgtct cgcgcgtttc ggtgatgacg gtgaaaacct ctgacacatg    2340
cagctcccgg agacggtcac agcttgtctg taagcggatg ccgggagcag acaagcccgt    2400
cagggcgcgt cagcgggtgt tggcgggtgt cggggctggc ttaactatgc ggcatcagag    2460
cagattgtac tgagagtgca ccatatgcgg tgtgaaatac cgcacagatg cgtaaggaga    2520
aaataccgca tcaggcggcc ttaagggcct cgtgatacgc ctatttttat aggttaatgt    2580
catgataata atggtttctt agacgtcagg tggcactttt cggggaaatg tgcgcggaac    2640
ccctatttgt ttatttttct aaatacattc aaatatgtat ccgctcatga caataaccc    2700
ctgataaatg cttcaataat attgaaaaag gaagagtatg agtattcaac atttccgtgt    2760
cgcccttatt ccctttttg  cggcattttg ccttcctgtt tttgctcacc cagaaacgct    2820
ggtgaaagta aaagatgctg aagatcagtt gggtgcacga gtgggttaca tcgaactgga    2880
tctcaacagc ggtaagatcc ttgagagttt tcgccccgaa gaacgttttc caatgatgag    2940
cacttttaaa gttctgctat gtggcgcggt attatcccgt attgacgccg ggcaagagca    3000
actcggtcgc cgcatacact attctcagaa tgacttggtt gagtactcac cagtcacaga    3060
aaagcatctt acggatggca tgacagtaag agaattatgc agtgctgcca taaccatgag    3120
tgataacact gcggccaact tacttctgac aacgatcgga ggaccgaagg agctaaccgc    3180
ttttttgcac aacatggggg atcatgtaac tcgccttgat cgttgggaac cggagctgaa    3240
tgaagccata ccaaacgacg agcgtgacac cacgatgcct gtagcaatgg caacaacgtt    3300
gcgcaaacta ttaactggcg aactacttac tctagcttcc cggcaacaat taatagactg    3360
gatggaggcg gataaagttg caggaccact tctgcgctcg gcccttccgg ctggctggtt    3420
tattgctgat aaatctggag ccggtgagcg tgggtctcgc ggtatcattg cagcactggg    3480
gccagatggt aagccctccc gtatcgtagt tatctacacg acggggagtc aggcaactat    3540
ggatgaacga aatagacaga tcgctgagat aggtgcctca ctgattaagc attggtaact    3600
gtcagaccaa gtttactcat atatacttta gattgattta aaacttcatt tttaatttaa    3660
aaggatctag gtgaagatcc ttttgataa  tctcatgacc aaaatccctt aacgtgagtt    3720
ttcgttccac tgagcgtcag accccgtaga aaagatcaaa ggatcttctt gagatccttt    3780
ttttctgcgc gtaatctgct gcttgcaaac aaaaaaacca ccgctaccag cggtggtttg    3840
tttgccggat caagagctac caactctttt tccgaaggta actggcttca gcagagcgca    3900
gataccaaat actgtccttc tagtgtagcc gtagttaggc caccacttca agaactctgt    3960
agcaccgcct acatacctcg ctctgctaat cctgttacca gtggctgctg ccagtggcga    4020
taagtcgtgt cttaccgggt tggactcaag acgatagtta ccggataagg cgcagcggtc    4080
gggctgaacg gggggttcgt gcacacagcc cagcttggag cgaacgacct acaccgaact    4140
gagataccta cagcgtgagc attgagaaag cgccacgctt cccgaaggga gaaaggcgga    4200
caggtatccg gtaagcggca gggtcggaac aggagagcgc acgagggagc ttccaggggg    4260
```

-continued

| | | |
|---|---|---|
| aaacgcctgg tatctttata gtcctgtcgg gtttcgccac ctctgacttg agcgtcgatt | 4320 |
| tttgtgatgc tcgtcagggg ggcggagcct atggaaaaac gccagcaacg cggccttttt | 4380 |
| acggttcctg gccttttgct ggccttttgc tcacatgttc tttcctgcgt tatccctga | 4440 |
| ttctgtggat aaccgtatta ccgcctttga gtgagctgat accgctcgcc gcagccgaac | 4500 |
| gaccgagcgc agcgagtcag tgagcgagga agcggaagag cgcccaatac gcaaaccgcc | 4560 |
| tctccccgcg cgttggccga ttcattaatg cagctggcac gacaggtttc ccgactggaa | 4620 |
| agcgggcagt gagcgcaacg caattaatgt gagttagctc actcattagg caccccaggc | 4680 |
| tttcactttt atgcttccgg ctcgtatgtt gtgtggaatt gtgagcggat aacaatttca | 4740 |
| cacaggaaac agct | 4754 |

<210> SEQ ID NO 11
<211> LENGTH: 4425
<212> TYPE: DNA
<213> ORGANISM: Homo sapiens

<400> SEQUENCE: 11

| | | |
|---|---|---|
| atggggaaga acaaactcct tcatccaagt ctggttcttc tcctcttggt cctcctgccc | 60 |
| acagacgcct cagtctctgg aaaaccgcag tatatggttc tggtccctc cctgctccac | 120 |
| actgagacca ctgagaaggg ctgtgtcctt ctgagctacc tgaatgagac agtgactgta | 180 |
| agtgcttcct tggagtctgt caggggaaac aggagcctct tcactgacct ggaggcggag | 240 |
| aatgacgtac tccactgtgt cgccttcgct gtcccaaagt cttcatccaa tgaggaggta | 300 |
| atgttcctca ctgtccaagt gaaaggacca acccaagaat ttaagaagcg gaccacagtg | 360 |
| atggttaaga cgaggacag tctggtcttt gtccagacag acaaatcaat ctacaaacca | 420 |
| gggcagacag tgaaatttcg tgttgtctcc atggatgaaa actttcaccc cctgaatgag | 480 |
| ttgattccac tagtatacat tcaggatccc aaaggaaatc gcatcgcaca atggcagagt | 540 |
| ttccagttag agggtggcct caagcaattt tcttttcccc tctcatcaga gcccttccag | 600 |
| ggctcctaca aggtggtggt acagaagaaa tcaggtggaa ggacagagca cccttcacc | 660 |
| gtggaggaat ttgttcttcc caagtttgaa gtacaagtaa cagtgccaaa gataatcacc | 720 |
| atcttggaag aagagatgaa tgtatcagtg tgtggcctat acacatatgg gaagcctgtc | 780 |
| cctggacatg tgactgtgag catttgcaga aagtatagtg acgcttccga ctgccacggt | 840 |
| gaagattcac aggcttctg tgagaaattc agtggacagc taaacagcca tggctgcttc | 900 |
| tatcagcaag taaaaccaa ggtcttccag ctgaagagga ggagtatga atgaaacttt | 960 |
| cacactgagg cccagatcca agaagaagga acagtggtgg aattgactgg aaggcagtcc | 1020 |
| agtgaaatca caagaaccat aaccaaactc tcatttgtga agtggactc acactttcga | 1080 |
| cagggaattc ccttctttgg gcaggtgcgc ctagtagatg ggaaaggcgt ccctatacca | 1140 |
| aataaagtca tattcatcag aggaaatgaa gcaaactatt actccaatgc taccacggat | 1200 |
| gagcatggcc ttgtacagtt ctctatcaac accaccaacg ttatgggtac ctctcttact | 1260 |
| gttagggtca attacaagga tcgtagtccc tgttacggct accagtgggt gtcagaagaa | 1320 |
| cacgaagagg cacatcacac tgcttatctt gtgttctccc caagcaagag ctttgtccac | 1380 |
| cttgagccca tgtctcatga actacctgt ggccatactc agacagtcca ggcacattat | 1440 |
| attctgaatg gaggcaccct gctggggctg aagaagctct ccttttatta tctgataatg | 1500 |
| gcaaagggag gcattgtccg aactgggact catggactgc ttgtgaagca ggaagacatg | 1560 |
| aagggccatt tttccatctc aatccctgtg aagtcagaca ttgctcctgt cgctcggttg | 1620 |

```
ctcatctatg ctgttttacc taccggggac gtgattgggg attctgcaaa atatgatgtt    1680
gaaaattgtc tggccaacaa ggtggatttg agcttcagcc catcacaaag tctcccagcc    1740
tcacacgccc acctgcgagt cacagcggct cctcagtccg tctgcgccct ccgtgctgtg    1800
gaccaaagcg tgctgctcat gaagcctgat gctgagctct cggcgtcctc ggtttacaac    1860
ctgctaccag aaaaggacct cactggcttc cctgggcctt tgaatgacca ggacgatgaa    1920
gactgcatca atcgtcataa tgtctatatt aatggaatca catatactcc agtatcaagt    1980
acaaatgaaa aggatatgta cagcttccta gaggacatgg gcttaaaggc attcaccaac    2040
tcaaagattc gtaaacccaa aatgtgtcca cagcttcaac agtatgaaat gcatggacct    2100
gaaggtctac gtgtaggttt ttatgagtca gatgtaatgg aagaggcca tgcacgcctg    2160
gtgcatgttg aagagcctca cacggagacc gtacgaaagt acttccctga catggatc    2220
tgggatttgg tggtggtaaa ctcagcaggg gtggctgagg taggagtaac agtccctgac    2280
accatcaccg agtggaaggc aggggccttc tgcctgtctg aagatgctgg acttggtatc    2340
tcttccactg cctctctccg agccttccag cccttctttg tggagcttac aatgccttac    2400
tctgtgattc gtggagaggc cttcacactc aaggccacgg tcctaaacta ccttcccaaa    2460
tgcatccggg tcagtgtgca gctggaagcc ctcccgcct tccttgctgt cccagtggag    2520
aaggaacaag cgcctcactg catctgtgca acgggcggc aaactgtgtc ctgggcagta    2580
accccaaagt cattaggaaa tgtgaatttc actgtgagcg cagaggcact agagtctcaa    2640
gagctgtgtg ggactgaggt gccttcagtt cctgaacacg gaaggaaaga cacagtcatc    2700
aagcctctgt tggttgaacc tgaaggacta gagaaggaaa caacattcaa ctccctactt    2760
tgtccatcag gtggtgaggt ttctgaagaa ttatccctga aactgccacc aaatgtggta    2820
gaagaatctg cccgagcttc tgtctcagtt ttgggagaca tattaggctc tgccatgcaa    2880
aacacacaaa atcttctcca gatgcccat ggctgtggag agcagaatat ggtcctcttt    2940
gctcctaaca tctatgtact ggattatcta aatgaaacac agcagcttac tccagaggtc    3000
aagtccaagg ccattggcta tctcaacact ggttaccaga acagttgaa ctacaaacac    3060
tatgatggct cctacagcac ctttggggag cgatatggca ggaaccaggg caacacctgg    3120
ctcacagcct ttgttctgaa gacttttgcc caagctcgag cctacatctt catcgatgaa    3180
gcacacatta cccaagccct catatggctc tcccagaggc agaaggacaa tggctgtttc    3240
aggagctctg ggtcactgct caacaatgcc ataaagggag gagtagaaga tgaagtgacc    3300
ctctccgcct atatcaccat cgcccttctg gagattcctc tcacagtcac tcaccctgtt    3360
gtccgcaatg cctgttttg cctggagtca gcctggaaga cagcacaaga agggaccat    3420
ggcagccatg tataccaa agcactgctg gcctatgctt ttgccctggc aggtaaccag    3480
gacaagagga aggaagtact caagtcactt aatgaggaag ctgtgaagaa agacaactct    3540
gtccattggg agcgccctca gaaacccaag gcaccagtgg ggcattttta cgaacccag    3600
gctccctctg ctgaggtgga gatgacatcc tatgtgctcc tcgcttatct cacgcccag    3660
ccagccccaa cctcggagga cctgacctct gcaaccaaca tcgtgaagtg atcacgaag    3720
cagcagaatg cccagggcgg tttctcctcc acccaggaca cagtggtggc tctccatgct    3780
ctgtccaaat atggagccgc cacatttacc aggactggga aggctgcaca ggtgactatc    3840
cagtcttcag ggcatttttc cagcaaattc caagtggaca caacaatcg cctgttactg    3900
cagcaggtct cattgccaga gctgcctggg gaatacagca tgaaagtgac aggagaagga    3960
```

-continued

```
tgtgtctacc tccagacctc cttgaaatac aatattctcc cagaaaagga agagttcccc    4020
tttgctttag gagtgcagac tctgcctcaa acttgtgatg aacccaaagc ccacaccagc    4080
ttccaaatct ccctaagtgt cagttacaca gggagccgct ctgcctccaa catggcgatc    4140
gttgatgtga agatggtctc tggcttcatt ccctgaagc caacagtgaa aatgcttgaa    4200
agatctaacc atgtgagccg gacagaagtc agcagcaacc atgtcttgat ttaccttgat   4260
aaggtgtcaa atcagacact gagcttgttc ttcacggttc tgcaagatgt cccagtaaga   4320
gatctcaaac cagccatagt gaaagtctat gattactacg agacggatga gtttgcaatc   4380
gctgagtaca atgctccttg cagcaaagat cttggaaatg cttga                   4425
```

PRODUCTION OF EUKARYOTIC PROTEINS AND NUCLEIC ACID MOLECULES IN C. ELEGANS

The present invention relates to the production of post-translationally modified eukaryotic proteins in general and human proteins in particular, in the nematode *Caenorhabditis elegans*. It also includes the production of post-translationally modified nucleic acid molecules, such as tRNA. It further includes the co-translational labeling of the expressed proteins with identifiable labels such as $^2$H, $^{13}$C, $^{15}$N, Se-methionine, Se-cystein or non-natural amino acids. Similarly the labeling of nucleic acid molecules with $^2$H, $^{13}$C and $^{15}$N.

BACKGROUND

There are several alternatives for the production of eukaryotic proteins in different expression systems. The following expression systems are currently in use.

Bacteria

Many *E. coli* expression systems are commercially available. Some examples are pET (Promega), pQE (Qiagen), pGEX (Amersham Pharmacia), ptrcHIS (Invitrogen), pDUAL (Stratagene). The advantage of *E. coli* systems are that they are cheap and very easy to use. The main disadvantage is that many eukaryotic proteins do not fold properly when expressed in *E. coli* and form insoluble aggregates. Codon usage is very different from that in higher eukaryotes. Often eukaryotic proteins must be modified following translation in order to be able to fold into the proper structure and/or to become activated. *E. coli* is not able to carry out complex post translational modifications such as acetylation, N- and O-linked glycosylation and, acylation and phosphorylation which are exclusively performed by eukaryotic cells.

The levels of expression vary enormously from protein to protein. The yield of recombinant protein from 1 liter of *E. coli* culture amounts typically to about 10 mg. In rare cases amounts of hundreds of milligrams of recombinant protein per liter *E. coli* culture can be obtained.

Yeast

The yeast *Pichia pastoris* is a well established system for expressing recombinant proteins. Several companies sell the relevant plasmid vectors. Invitrogen Corp. for example sells the pPIC set of plasmids. The advantages of *Pichia* is that being a eukaryote, the post-translational modifications are more similar to those that occur in humans or higher eukaryotes. *Pichia* is easy and fast to transform. It is also easy to grow on a large scale. Expression levels vary considerably. Levels as high as 12 grams/liter have been reported.

Insect Cells

Insect cells can also be used to express recombinant proteins. Several companies sell the relevant plasmid vectors and cell lines. Invitrogen's systems are DES, InsectSelect and MaxBac. The advantages of insect cells are that, being multicellular eukayotes, insects are much more like humans than yeast are. The disadvantages are (i) insect cells are much more difficult to grow and maintain than bacterial or yeast cells (ii) they are more expensive to cultivate (iii) they require sterile incubators (iv) the expression levels are much lower than those seen with the yeast or bacterial systems.

Human Cell Lines

Human cell lines can also be used, but they require growth factors in order to keep them alive. Today, human growth factors are very expensive, and this makes human cell lines bad candidates for e.g. growth factor production.

Nematodes

Nematodes, small roundworms, are one branch of eukaryotic organisms that have so far not been exploited for large-scale protein or nucleic acid production. Nematodes are very simple animals and have served as a developmental model system ever since 1949 (Dougherty E C and Nigon V., *J. Parasitol*. (1949) 35, 11; Brenner S in a letter to Max Perutz, 5 Jun. 1963). Especially the development of each of the 959 cells in the nematode *C. elegans* is well characterized and its entire genome was recently sequenced and is now publicly available ("The *C. elegans* Sequencing Consortium" Genome Sequence of the nematode *C. elegans*: A platform for investigating biology. *Science* (1998) 282, 2012-2018). Nematodes are eukaryotic organisms that are genetically much more closely related to humans than bacteria, about 60% of their proteins are homologous to human proteins.

What makes nematodes interesting as a protein expression system for production of eukaryotic and in particular human proteins is the fact that they are equipped with the necessary machinery to perform post-translational modifications on proteins. Hence, proteins (peptide drugs) produced in nematodes are virtually identical to the natural human proteins and as a result may have fewer undesirable side effects and a higher specific activity requiring lower dosages. Other advantages of the nematode expression system include high yields of expressed protein, its low maintenance costs, its ease of use and that one can easily scale up the production.

Expression of human beta-amyloid peptide in transgenic *C. elegans* to produce muscle-specific deposits immunoreactive with anti-beta-amyloid polyclonal and monoclonal antibodies has been described by C. D. Link (Link C. D., Expression of human beta-amyloid peptide in transgenic *Caenorhabditis elegans*, Proc. Natl. Acad. Sci. (1 995) 92,9368-9372), and he suggests that his invertebrate model may be useful for in vivo investigation of factors that modulate amyloid formation.

The international patent application WO 00/54815 discloses expression of DNA or proteins in *C. elegans* by using an expression vector comprising a promoter that directs the gene expression to the excretory cell of *C. elegans*. The reason for the protein expression is not production and isolation of a protein but for discovery of novel molecules, i.e. drugs, involved in the cell motility, cell shape and cell outgrowth process, and to establish their function.

DESCRIPTION OF THE INVENTION

The present invention provides an in vivo expression system for production of eukaryotic, such as human, proteins and nucleic acid molecules that is easy to handle, inexpensive, genetically stable and easy to scale up. The nematode expression system of the invention is suitable for the large-scale production of ultra pure recombinant human proteins. Proteins and nucleic acid molecules produced will contain all the modifications that are typical for higher organisms (eukaryotes), such as acetylation, N- and O-linked glycosylation and, acylation, phosphorylation and cleavage of signal sequences etc. These modifications are crucial for the specificity of a medically interesting protein in signaling pathways.

The novel nematode protein expression system combines the advantages of eukaryotic cells such as post-translational modifications with the simplicity of handling known from *E. coli* fermentation.

The expression system comprises the nematode *Caenorhabditis elegans*. Since the number of different plasmids that can be simultaneously injected into *C. elegans* is in excess of twenty, this enables the simultaneous expression of multiple plasmids harboring e.g. different subunits of large complexes containing proteins and/or nucleic acids.

Examples of eukaryotic proteins that may be produced on an industrial scale with the present invention include: human growth factors, growth factor receptors (membrane bound or soluble part) for basic research on stem cells and for medical applications such as stem cell based treatment of heart disease, diabetes, cancer, and diseases of the nervous system, including Parkinson's and Alzheimer's disease. In addition monoclonal antibodies, G-proteins, G-protein coupled receptors, and large, multi-subunit protein-RNA complexes such as polymerases, telomerase and splicing factor complexes. Beside potential medical applications, the produced proteins and nucleic acids can be used for structure characterization by X-ray crystallography, electron crystallography or NMR where one studies post-translational modified proteins and nucleic acids. The C. elegans expression system can also be used for labeling of eukaryotic proteins with $^2$H, $^{13}$C, $^{15}$N, Se-Met, Se-Cys or non-natural amino acids for crystallographic applications or with $^2$H, $^{13}$C, or $^{15}$N, for NMR experiments.

One aspect of the present invention is directed to a plasmid vector for expression in *Caenorhabditis elegans* comprising in the 5' to 3' direction of transcription operably linked to each other a heat shock promoter nucleotide sequence, a synthetic intron nucleotide sequence optionally containing a Shine-Dalgarno sequence for efficient shuttling between *C. elegans* and *E. coli*, optionally a nucleotide sequence coding for a nuclear localisation signal or a secretion signal, e.g selected from naturally occurring signal sequences, such as from *C. elegans* or the signal sequence of the protein or nucleic acid molecule that is to be expressed, a nucleotide sequence coding for a recognisable tag, optionally a nucleotide sequence coding for a fluorescent protein, a nucleotide sequence coding for a protease cleavage site, a multiple cloning site containing a nucleotide sequence coding for an eukaryotic, such as human, protein or a nucleic acid molecule, and a nucleotide sequence coding for termination of translation.

The nucleotide sequence order in the plasmid may be modified so that the multiple cloning site is followed by the nucleotide sequence coding for a protease cleavage site, the optional nucleotide sequence coding for a fluorescent protein, optionally the nucleotide sequence coding for a nuclear localization signal or a secretion signal and the nucleotide sequence coding for a recognizable tag.

Examples of the nucleotide sequence coding for a protease cleavage site include cleavage sites for the proteases TEV, Thrombin and Factor Xa.

In an embodiment of the plasmid vector, the synthetic intron nucleotide sequence contains the Shine-Dalgarno sequence AGGAG, the nucleotide sequence coding for a nuclear localization signal is SEQ ID NO: 3, the sequence coding for a recognizable tag is a sequence coding for a 6-His tag, a 10His tag or a 12-His tag, i.e. 6, 10 or 12 histidine residues that enable easy purification on Ni chelating columns, the nucleotide sequence coding for a fluorescent protein is a nucleotide sequence coding for the green fluorescent protein with the sequence SEQ ID NO: 8, the nucleotide sequence coding for a protease cleavage site is a sequence coding for a protease cleavage site, that enables later cleaving off of the 6, 10 or 12 histidine residues.

In a preferred embodiment the plasmid, lacking a nucleotide sequence coding for an eukaryotic protein or a nucleic acid molecule, has the nucleotide sequence SEQ ID NO: 1. The plasmide has no nucleotide sequence coding for a nuclear localization signal. The artificial intron starts at 480 and ends at 521, (gtatgtttcga atgatactaa cataacatag aacattttca g), then follows the 6-His-tag sequence, 547 to 564, (cat cac cat cac cat cac), and a linker sequence, 565 to 594, connects the His-tag to the sequence coding for the TEV protease recognition site: 595 to 618. Then comes the multiple cloning site (MCS)(start at 619).

In another preferred embodiment the plasmid, lacking a nucleotide sequence coding for an eukaryotic protein or a nucleic acid molecule, has the nucleotide sequence SEQ ID NO: 2. The artificial intron starts at 480 and ends at 521 (gtatgtttcga atgatactaa cataacatag aacattttca g), then follows the nucleotide sequence coding for a nuclear localisation signal(NLS): start at pos 533, end at 580 (ctagtgctca gaaaaaatga ctgctccaaa aagaagcgt aaggtgcc). After the NLS comes the 6-His-tag sequence 588 to 605 (catcaccatc ccatcac). A linker sequence (606 to 635) connects it to the sequence coding for the TEV protease recognition site: 636 to 656, which is followed by the multiple cloning site (start at 658).

For cloning purposes, the NLS used in the plasmids is a bit longer than the essential NLS DNA sequence. (The NLS was cloned into the plasmid pre-cut with the restriction enzymes Nhel and Ncol). The essential NLS sequence (558 to 568: ccaaagaagaagcgtaaggtgcc c, [the last c comes from the Ncol cut vector]) translates into the protein sequence PKKKRKV, that is recognized by the nuclear import machinery.

The nuclear localization signal, NLS, is useful for the following reason. When the nematodes are heat shocked and in such a way forced to over-produce the desired human proteins, it may be safer to direct the produced protein into the cell nucleus. This is exactly what the NLS does. The advantage of transporting proteins into the nucleus is that there are no proteases present. These proteases can be present in the cytoplasm and proteases are especially concentrated in organelles called lysosomes. By using a NLS to send the expressed proteins into the nucleus, they are transported in one piece away from potentially dangerous proteases.

The DNA sequence of the green fluorescent protein, GFP, contains additionally three introns in the version in SEQ ID NO: 8. It is primarily used as a luminescent marker to "visualize" that *C. elegans* expresses the desired protein(s). In the plasmids where it is present, it follows the 6His-tag: e.g. 6His-GFP-TEV-MCS when incorporated into plasmid SEQ ID NO: 1, or NLS-6His-GFP-TEV-MCS when incorporated into plasmid SEQ ID NO: 2.

In yet another preferred embodiment the plasmid, lacking a nucleotide sequence coding for an eukaryotic protein or a nucleic acid molecule, has the nucleotide sequence SEQ ID NO: 9. The order of the sequences in the plasmid is modified in relation to the sequences in the plasmid SEQ ID NO:1 and the green fluorescent protein with the sequence SEQ ID NO: 8 is included. The sequences come in the order MCS-TEV-GFP-6His.

In still another preferred embodiment the plasmid, lacking a nucleotide sequence coding for an eukaryotic protein or a nucleic acid molecule, has the nucleotide sequence SEQ ID NO:10. The order of the sequences in the plasmid is modified in relation to the sequences in the plasmid SEQ ID NO: 2 and the green fluorescent protein with the sequence SEQ ID NO: 8 is included. The sequences come in the order MCS-TEV-GFP-NLS-6His.

Inserting the green fluorescent protein (GFP) after the multiple cloning site (MCS) makes it possible to have a fast check for proper protein folding. If the expressed protein of interest, such as a human growth factor, does not fold properly, it will not allow the green fluorescent protein that follows after to fold properly either and as a consequence one does not see green fluorescence. This is a fast test for protein folding. In addition, GFP can be used as a purification tag, either by using ion exchange chromatography following established GFP protocols, or as an affinity tag using immobilized anti-GFP anti-bodies.

The preferred plasmids of the invention are intend to be used in *E. coli* as well. Therefore they are designed as "shuttle vectors". The only modification to the above disclosed plasmid sequences is that a so-called "Shine-Dalgarno" sequence is centered about 10 nucleotides before the start codon of transcription, ATG. The Shine-Dalgarno sequence, AGGAG, is a translational initiation signal for *E. coli* and does not affect *C. elegans*.

Thus, in plasmid SEQ. ID NO: 1 the Shine-Dalgarno sequence is centered 10 nucleotides before the ATG-6His; in plasmid SEQ ID NO: 2 the Shine-Dalgarno sequence is centered 10 nucleotides before the ATG-NLS; and in plasmids SEQ ID NO: 9 and 10 the Shine-Dalgarno sequence is centered 10 nucleotides before the MCS (the MCS contains an ATG).

The plasmids SEQ ID NO: 1, 2, 9 and 10 contain a protein that makes *E. coli* bacteria resistant to antibiotica, e.g. ampicillin or carbicillin or to kanamycin. However, these proteins have no effect on *C. elegans* (e.g. they do not provide any antibiotica resistance to *C. elegans*).

In a most preferred embodiment of the invention the nucleotide sequence coding for a human protein is a sequence coding for a human growth factor protein. Specific examples of some human growth factor proteins are:

SEQ ID NO: 4, the sequence of a growth factor called Wnt2b (*Homo sapiens* wingless-type MMTV integration site family, member 2B), SEQ ID NO: 5, the sequence of a growth factor called FGF10 (*Homo sapiens* keratinocyte growth factor 2 (FGF10)), SEQ ID NO: 6, the sequence of a growth factor called KLS (*Homo sapiens* KIT ligand soluble fraction), and SEQ ID NO: 7, the sequence of a growth factor called BMP10 (*Homo sapiens* bone morphogenetic protein 10).

Another aspect of the invention is directed to a method of producing eukaryotic such as human, proteins or nucleic acid molecules in nematodes comprising the steps of injecting one or several plasmid vectors, preferably simultaneously, according to the invention into the gonad of *C. elegans* hemaphrodites, cultivating the nematodes in a growth medium at a temperature of below 25° C., followed by shifting the growth temperature to values between 30 and 33° C. for induction of protein or nucleic acid molecule expression in several hundred somatic cells, with highest expression levels in neuronal and epidermal cells, and isolating the eukaryotic proteins or nucleic acid molecules from said cells.

In an embodiment of the method of the invention the growth medium comprises bacteria, such as *E. coli*, as feed for the nematodes. Since *C. elegans* can feed exclusively on bacteria dispersed in minimal media, this fact can be exploited to label proteins produced in *C. elegans*. By feeding the worms bacteria that were previously labeled (e.g. with $^2$H, $^{13}$C, $^{15}$N, Se-Met, Se-Cys or certain non-natural amino acids for expression of proteins and $^2$H, $^{13}$C and $^{15}$N for expression of nucleic acid molecules) according to existing protocols, the respective label will be incorporated into newly produced proteins and nucleotides.

In a preferred embodiment the isolation is performed, in case the plasmid includes a nucleotide sequence coding for a nuclear localization signal, by carefully opening the cells of the nematodes, e.g. by using a "bead beater" (=a blender filled with small zirconium beads)—thereby leaving the cell nuclei intact which contain the expressed proteins or nucleic acid molecules. This is followed by separating the cell nuclei and by dissolving the nuclear membrane to release the expressed proteins and subjecting the mixture to chromatographic purification. For proteins this includes a stationary phase specifically binding to the recognizable tag, e.g. 10His-tagged protein to Ni-chelating beads packed into a purification column, followed by washing off unspecifically bound proteins, and elution under conditions releasing the eukaryotic, such as human, protein-from the column e.g. an imidazole gradient that releases the 10-His-tagged protein. The recognizable tag is then cleaved off by supplying the specific protease corresponding to the protease cleavage site encoded by the plasmid used and having an uncleavable recognizable tag, such as a 6-His-tag, and at the same time performing dialysis against a low concentration of the agent that releases the tag from the stationary phase, (suitably about 10-50 mM if the elution was done with 400-700 mM imidazole), transferring the cut mixture containing the eukaryotic protein with the cut off tag and the protease that itself has an uncleavable recognizable tag, e.g. 6-His-tag, onto a fresh tag specific column, eluting the column to obtain an eluate containing the eukaryotic protein leaving the cut off recognizable tag, e.g. 10-His tag, and recognizably tagged, e.g. 6-His-tagged protease bound to the stationary phase.

In another preferred embodiment the isolation is performed, in case the plasmid lacks a nucleotide sequence coding for a nuclear localisation signal, by mashing the nematodes, to release the expressed eukaryotic proteins and subjecting the mixture to chromatographic purification with a stationary phase specifically binding to the recognizable tag, followed by washing and elution under conditions releasing the eukaryotic protein from the stationary phase, as exemplified in the preceding paragraph.

In case the plasmid used lacks a nuclear localization signal, or an extra precaution to prevent the eukaryotic protein from being attacked by unspecific proteases that can be present in the cell is desired, e.g. for cases where the proteins are degradation sensitive, an alternative or complementary way of protecting the expressed proteins against protease degradation is to inject a separate plasmid, e.g. SEQ ID NO:1 or 2 lacking the nucleotide sequence coding for a protease cleavage site, and containing a nucleotide sequence coding for a general protease inhibitor, such as alpha2-Macroglobulin (α2-M), SEQ ID NO: 11.

Thus, in an additionally preferred embodiment of the method of the invention, the method comprises additionally injecting a plasmid vector comprising operably linked to each other a heat shock promoter nucleotide sequence, a synthetic intron nucleotide sequence optionally containing a Shine-Dalgarno sequence, optionally a nucleotide sequence coding for a nuclear localisation signal, a nucleotide sequence coding for a recognisable tag, optionally a nucleotide sequence coding for a fluorescent protein, a nucleotide sequence coding for a general protease inhibitor, such as the general protease inhibitor SEQ ID NO:11 coding for α2-Macroglobulin, and a nucleotide sequence coding for termination of translation, for co-expression of the general protease inhibitor. In this case, the recognisable tag remains on the expressed general protease inhibitor and it will be bound to the tag specific column (together with the (e.g. 6-His-) tagged protease and the cleaved off (e.g. 10-His-) tag from the eukaryotic protein in the second and last specific column step).

The *C. elegans* expression system, including the plasmids and the method of producing eukaryotic, such as human, proteins or nucleic acid molecules in nematodes of the invention, is particularly suitable for large scale production of ultra-pure recombinant eukaryotic proteins, in particular human growth factors. Proteins produced will contain the modifications that are typical for higher organisms (eukaryotes), such as acetylation, N- and O-linked glycosylation and, acylation, phosphorylation and cleavage of signal sequences etc. These modifications are crucial for the specificity of a medically interesting protein in signalling pathways. Examples of human (eukaryotic) proteins that may be produced on an industrial scale with the present invention include: human growth factors, growth factor receptors (membrane bound or soluble part) for basic research on stem cells and for medical applications. In addition monoclonal antibodies, G-proteins, G-protein coupled receptors. In particular, the system is designed to allow for shuttling between C. elegans and E. coli in order to study the effects of post-translational modifications. It also allows the labelling of C. elegans produced proteins and nucleic acid molecules with identifiable markers (e.g. $^2$H, $^{13}$C, $^{15}$N, Se-Met, Se-Cys, etc.) for NMR and X-ray crystallographic studies, by feeding the nematodes with pre-labelled bacteria. Further, the expression of eukaryotic proteins, such as human, proteins or nucleic acid molecules in C. elegans can be directed to the protective protease reduced environment of the cell nucleus or to certain compartments of the cell, depending on the chosen signal peptide. The system also allows simultaneous expression of proteins from more than 20 plasmids if the reconstruction of large, multi-subunit protein-RNA complexes such as polymerases, telomerase and splicing factor complexes is required.

The invention will now be further illustrated by description of experiments, and it should be understood that the scope of the claims is not restricted to any specifically mentioned details.

Experiments

All manipulations of C. elegans worms were performed using techniques described in Methods in Cell Biology, vol 84; Caenorhabditis elegans: modern biological analysis of an organism, ed. Epstein and Shakes, Academic Press, 1995, or using minor modifications of the methods described therein.

Transgenic C. elegans strains were constructed by injection of plasmid DNA into worms of the genotype unc-36 (e251); hmp-1-(zu278)/daf-11(m8ts)sma-1(e30) together with plasmids encoding unc-36(+) and hmp-1(+) (Costa et al., Journal of Cell Biology 141: 297-308 1998). hmp-1 (zu278) causes an embryonic lethal phenotype (Costa et al. 1998). Lines were established of the genotypes unc-36 (e251); hmp-1(zu278); svEx[unc-36(+) hmp-1(+) hs-gen-1 (+)] where 'gen-1' denotes the gene encoding the human growth factor.

Worms were heat shocked at 33° C. for two hours by using established procedures. (Stringham E G and Candido, E P M Environmental Toxicology and Chemistry 13: 1211-1220 1994).

Expression Vector Construct

In order to express proteins in C. elegans we have built four plasmid vectors based on the plasmide pPD49,78-umu, SEQ ID NO: 1,2,9 and 10, that allows the heat inducible expression of genes in many different cells. The vector contains a C. elegans heat shock promoter for the ectopic expression of foreign proteins. The promoter is inactive below 25° C. However, shifting the growth temperature to values between 30 and 33° C. results in induction of protein expression at high level in several hundred somatic cells with highest expression levels in neuronal and epidermal cells.

The vectors are designed to make translational fusions. Downstream of the ATG is a sequence encoding a 6-His-tag followed by a TEV protease cleavage site and a multiple cloning site in plasmids SEQ ID NO: 1 and 2.

Micro-injection and Selection

In order to determine the expression level of single protein, we generated several plasmids each containing a different test gene together with appropriate genetic selection markers on separate plasmids.

We injected plasmids into hermaphrodites of the genotype unc-36(e251); hmp-1 (zu278)/daf-11 (m8ts)sma-1(e30) together with plasmids encoding unc-36(+) and hmp-1(+). hmp-1(zu278) causes an embryonic lethal phenotype (Costa et al. 1998). Lines were established of the genotypes unc-36 (e251); hmp-1(zu278); svEx[unc-36(+) hmp-1(+) hs-gen-1 (+)] where 'gen-1' denotes the gene to be tested.

Recombination between different plasmids of more then 600 bp occurs in vivo and transformed first generation F1 progeny are obtained in which the different injected plasmids together form an episome (referred to as an extrachromosomal array). Approximately 1 in 10 F1 transformants give rise to stable lines in which the extrachromosomal array is transmitted from generation to generation without change. Extrachromosomal arrays are relatively stable mitotically so that in any one transformed animal most cells contain the array. By using appropriate co-injection markers encoding essential genes it is possible to obtain strains in which all adult and larval worms in the population contain the array.

Protein Expression

C. elegans is grown from liquid medium in Erlenmeyer flasks on a temperature controlled shaker at 20° C. The liquid growth medium contains the slow growing E. coli strain OP50 on which the nematodes feed. The worms are grown during 7 days after which shifting the growth temperature from 20° C. to 33° C. induces protein production under the control of a heat shock promoter.

The yield of wet worms grown from one liter of initial culture is about 10 g. The green fluorescence protein (GFP) is expressed in about 25% of the cells and leads to a visible florescence signal that is seen under the fluorescence light microscope.

The yield of pure protein from a starting material of 10 to 20 g cultured and induced worms is roughly 0.2 to 1.0 mg.

The human growth factor called Wnt2b (Homo sapiens wingless-type MMTV integration site family, member 2B), was successfully expressed in the worms from the plasmide SEQ ID NO: 1 comprising in the multiple cloning site the nucleotide sequence SEQ ID NO: 4.

In short, the nematodes are grown from simple liquid medium. They grow in 25 fermenters or in Erlenmeyer flasks. The worms have a generation time of about 2-3 days and adult worms grow to about 1 mm in length. Each hermaphrodite produces about 300-500 eggs per generation. They can be repeatedly stored for long periods of time at −80° C. Stable lines can be selected after injection of up to twenty different plasmids into the gonad of hemaphrodites.

The invention claimed is:

1. Plasmid vector for expression in *Caenorhabditis elegans* and in *Escherichia coli* comprising in the 5' to 3' direction of transcription operably linked to each other a heat shock promoter nucleotide sequence, a synthetic intron nucleotide sequence containing a Shine-Dalgarno sequence, optionally a nucleotide sequence coding for a nuclear localization signal or a secretion signal, a nucleotide sequence coding for a recognizable tag, optionally a nucleotide sequence coding for a fluorescent protein, a nucleotide sequence coding for a protease cleavage site, a multiple cloning site containing a nucleic acid molecule or a nucleotide sequence coding for a eukaryotic protein, and a nucleotide sequence coding for termination of translation so as to express a eukaryotic protein or nucleic acid molecule in *Caenorhabditis elegans* and in *Escherichia coli* wherein the synthetic intron nucleotide sequence contains the Shine-Dalgarno sequence AGGAG, the nucleotide sequence coding for a nuclear localization signal is SEQ ID NO: 3, the sequence coding for a recognizable tag is a sequence coding for a 6-Histidine (His), 10-His or 12-His tag, the nucleotide sequence coding for a fluorescent protein is a nucleotide sequence coding for the green fluorescent protein with the sequence SEQ ID NO: 8, the nucleotide sequence coding for a protease cleavage site is a sequence coding for a Tobacco Etch Virus (TEV) protease cleavage site.

2. Plasmid vector according to claim 1, wherein the nucleotide sequence order is modified so that the multiple cloning site is followed by the nucleotide sequence coding for a protease cleavage site, the optional nucleotide sequence coding for a fluorescent protein, optionally the nucleotide sequence coding for a nuclear localization signal or a secretion signal and the nucleotide sequence coding for a recognizable tag.

3. Plasmid vector for expression in *Caenorhabditis elegans* and in *Escherichia coli* comprising in the 5' to 3' direction of transcription operably linked to each other a heat shock promoter nucleotide sequence, a synthetic intron nucleotide sequence containing a Shine-Dalgarno sequence, optionally a nucleotide sequence coding for a nuclear localization signal or a secretion signal, a nucleotide sequence coding for a recognizable tag, optionally a nucleotide sequence coding for a fluorescent protein, a nucleotide sequence coding for a protease cleavage site, a multiple cloning site containing a nucleic acid molecule or a nucleotide sequence coding for a eukaryotic protein, and a nucleotide sequence coding for termination of translation so as to express a eukaryotic protein or nucleic acid molecule in *Caenorhabditis elegans* and in *Escherichia coli* wherein the plasmid, lacking a nucleotide sequence coding for a eukaryotic protein or a nucleic acid molecule, has the nucleotide sequence SEQ ID NO: 1 or SEQ ID NO:2.

4. Plasmid vector for expression in *Caenorhabditis elegans* and in *Escherichia coli* comprising in the 5' to 3' direction of transcription operably linked to each other a heat shock promoter nucleotide sequence, a synthetic intron nucleotide sequence containing a Shine-Dalgarno sequence, a multiple cloning site containing a nucleic acid molecule or a nucleotide sequence coding for a eukaryotic protein, a nucleotide sequence coding for a protease cleavage site, optionally a nucleotide sequence coding for a fluorescent protein, optionally a nucleotide sequence coding for a nuclear localization signal or a secretion signal, a nucleotide sequence coding for a recognizable tag and a nucleotide sequence coding for termination of translation so as to express a eukaryotic protein or nucleic acid molecule in *Caenorhabditis elegans* and in *Escherichia coli* wherein the plasmid, lacking a nucleotide sequence coding for a eukaryotic protein or a nucleic acid molecule, has the nucleotide sequence SEQ ID NO:9 or SEQ ID NO:10.

5. Plasmid vector according to claim 1, wherein the plasmid, lacking a nucleotide sequence coding for a eukaryotic protein or a nucleic acid molecule, has the nucleotide sequence SEQ ID NO: 1.

6. Plasmid vector according to claim 1, wherein the plasmid, lacking a nucleotide sequence coding for a eukaryotic protein or a nucleic acid molecule, has the nucleotide sequence SEQ ID NO: 2.

* * * * *